United States Patent [19]

Metals

[11] Patent Number: 4,688,553

[45] Date of Patent: Aug. 25, 1987

[54] FILTER, PARTICULARLY FOR TRAPPING BLOOD CLOTS

[75] Inventor: Joël Metals, La Cottenciere, France

[73] Assignee: L. G. Medical S.A., France

[21] Appl. No.: 797,848

[22] Filed: Nov. 14, 1985

[30] Foreign Application Priority Data

Nov. 29, 1984 [FR] France .................. 84 18198

[51] Int. Cl.4 ...................... A61B 17/00; A61M 29/00
[52] U.S. Cl. ................ 128/1 R; 128/303 R; 128/325; 128/345
[58] Field of Search ............ 128/1 R, 325, 345

[56]  References Cited

U.S. PATENT DOCUMENTS 4,643,184  2/1987  Mobin-Uddin ............... 128/303 R

Primary Examiner—Dalton L. Truluck
Attorney, Agent, or Firm—Steinberg & Raskin

[57] ABSTRACT

The invention relates to an improved filter intended to be placed in the blood stream for the trapping of clots. The filter (10) of the invention is characterised in that it comprises legs (12) provided with appendices (14) which allow centering of the filter inside a vein (6).

The invention is applied to filters intended to be placed in veins with a view to avoiding emboli.

16 Claims, 12 Drawing Figures

FILTER, PARTICULARLY FOR TRAPPING BLOOD CLOTS

BACKGROUND OF THE INVENTION

The object of the invention is an improved filter intended to be placed in the blood stream, particularly in a section of vein, in order to trap blood clots.

Filters of this type are known and are for example described in U.S. Pat. No. 3,952,747 and in the French Patent Application EN 84 14144 filed on Sept. 14, 1984.

Generally speaking, these filters take the form of a small frustoconical basket which is hooked inside a vein downstream of the section which it is desired to filter; generally this is the vena cava which arrives at the heart. And so, before they enter the heart, it is possible to trap any blood clots which may form and which may lead to the formation of emboli.

One difficulty inherent in this type of operation is that of correctly positioning the filter with its axis substantially in the axis of the vein into which it is to be hooked. To facilitate this fitting, the legs of the filter are normally provided with hooks. Normally, in order to insert the filter into the vein, it is pushed in by means of a tube which traverses the vein and the diameter of which is less than that of the vein. When the filter arrives at the end of the tube, it is therefore left in the vein and expansion of its hook-shaped legs provides for anchoring of the filter. The evidence shows that being left in place in this way is, in practice, extremely difficult to monitor. In fact there is scarcely any chance of the basket-like filter occupying, inside the vein, what is the most favourable position, with its axis substantially parallel with the axis of the vein.

SUMMARY OF THE INVENTION

The object of the invention is to overcome this difficulty.

To this end, a filter according to the invention, of the type formed by flexible legs deployed substantially in a conical corolla and emanating from an ogival head, is characterised in that at least some of the aforesaid legs are, towards their free ends, provided with appendices orientated substantially parallel with the substantially cylindrical wall described by a generatrix parallel with the axis of the said conical corolla and describing as a directive line the opening perimeter of the corolla in a normal position of use.

In this way, when the filter is inserted into the vein, the appendices are applied against the walls of the vein and compel the filter to adopt a position with its axis substantially coincident with the axis of the vein.

According to a preferred embodiment of the invention, the filter comprises at least three legs provided with the aforesaid appendices and distributed angularly about the axis of the filter. In this way, satisfactory automatic centering of the filter is achieved when this is placed in position in the vein.

According to a characteristic of a preferred embodiment of the invention, the legs provided with appendices are shorter than those which are not. In this way, when the filter is introduced into the vein, the legs which are provided with appendices are the first to be applied against the inner wall of the vein and so center the filter before the other longer legs are deployed and become hooked into the inside wall of the vein.

BRIEF DESCRIPTION OF THE DRAWING

The invention and the way it is applied will become more clearly evident from the ensuing description which is given with reference to the appended drawings, in which.

DESCRIPTION OF THE PREFERRED EMBODIMENTS

Figure 1:
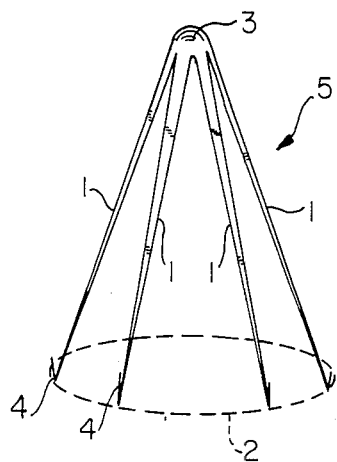
FIG. 1 shows diagrammatically and in perspective a conventional filter produced in accordance with the prior art.
Figure 2:
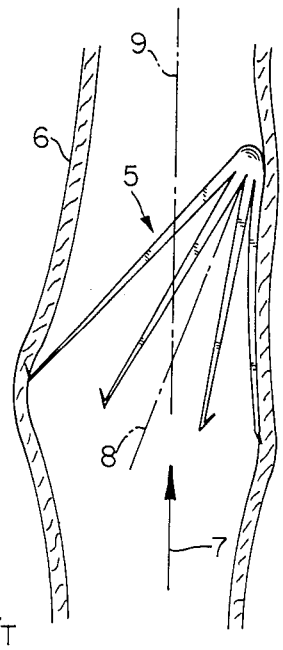
FIG. 2 diagrammatically shows the filter positioned inside a vein, this filter being blocked across the vein and not parallel with its axis.
Figure 3:
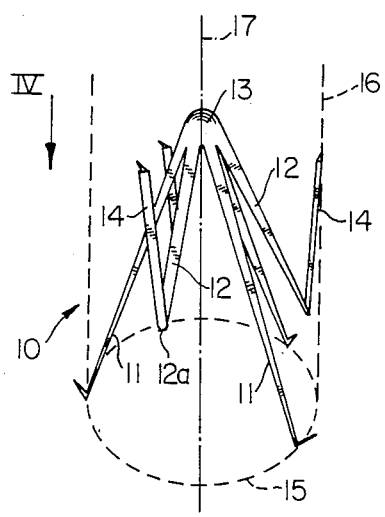
FIG. 3 is a view, like FIG. 1, and showing a filter modified in accordance with the invention.

With reference firstly to FIGS. 1 and 2, a filter 5 according to the prior art consists essentially of legs 1, for example four in number and deployed substantially according to a conical corolla, the opening of which is marked by dotted lines at 2, its legs emanating from a common ogival head 3. The legs finish at their free ends in hooks 4.

The positioning of such a filter inside a vein is known and currently practiced. It is possible for example to refer in this respect to the description given in the aforementioned Patent Application No. 84 14 144.

FIG. 2 shows the filter 5 which has been located inside a vein 6, the direction of blood flow being indicated by the arrow 7. As often happens, the filter is positioned with its axis 8 clearly crosswise in relation to the axis 9 of the vein, which does not allow the filter to work under the best of conditions.

Referring to FIGS. 3 to 6, it will be seen that a filter modified according to the invention, generally identified by reference numeral 10, comprises two different types of legs. In the example shown, the filter comprises three legs 11 which may be constituted identically to the legs 1 of the filter 5 in FIGS. 1 and 2, and three shorter legs 12, the legs 11 and 12 emanating from an ogival head 13. As emerges clearly from FIGS. 3 and 5, the short legs 12 are towards their free ends provided with appendices 14 which fold substantially backwards towards the tip of the cone 13. In other words, the appendices 14 point from the ends 12a of the legs 12 towards the closure side of the cone which the filter forms.

Figure 5:
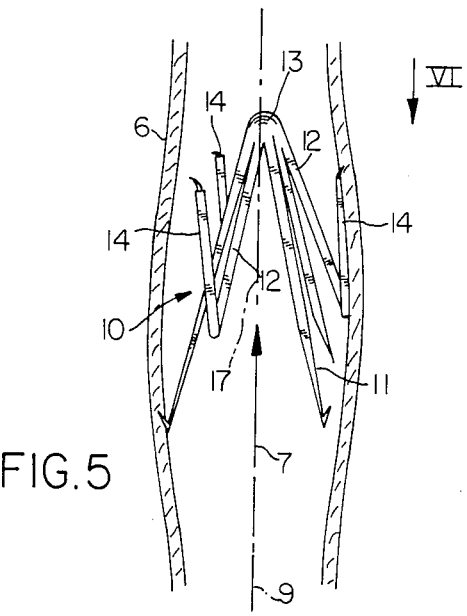
FIG. 5 is a view, like FIG. 2, and showing the modified filter of the invention positioned in a vein and of which the axis coincides substantially with that of the vein.
Figure 4:
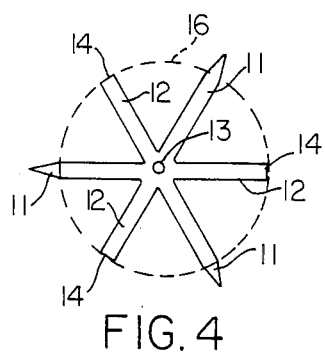
FIG. 4 is a plan view according to the arrow IV in FIG. 3.

To be more precise, if reference numeral 15 denotes the opening perimeter of the corolla which the filter forms and if 16 is used to designate the cylinder engendered by a generatrix parallel with the axis 17 of the cone formed by the filter 10 and describing the line 15 as it moves, the appendices 14 are directed in such a way as to be substantially parallel with the wall of the cylinder 16. In other words, when the filter is in place in the vein 6, as shown in FIG. 5, the appendices 14 are applied against the inside wall of the vein 6, so automatically centering the axis 17 of the filter 10 on the axis 9 of the vein 6. Indeed, the cylinder 16 and the vein 6 substantially coincide, the curve 15 having been defined as the perimeter of the opening corolla of the filter in its normal position of use.

Figure 7:
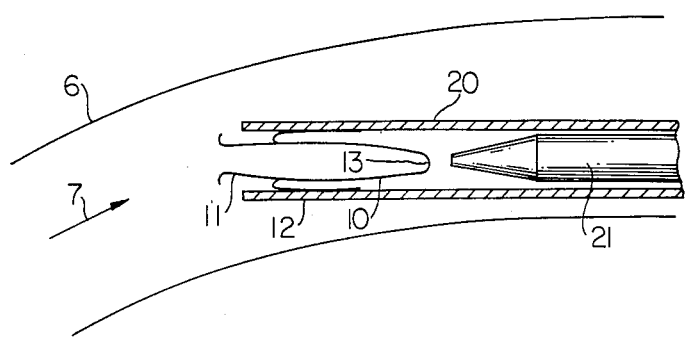
FIGS. 7, 8 and 9 respectively show three successive stages in the positioning of the filter according to the invention in a vein, taken respectively on the lines VII-VIII and IX—IX in FIG. 6.
Figure 8:
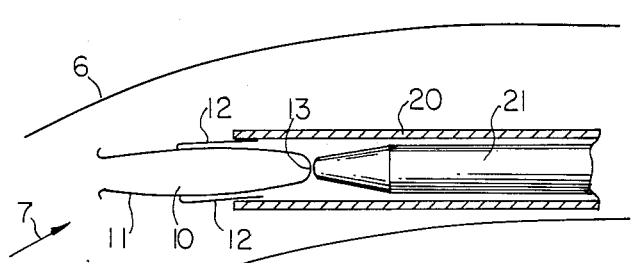
Figure 9:
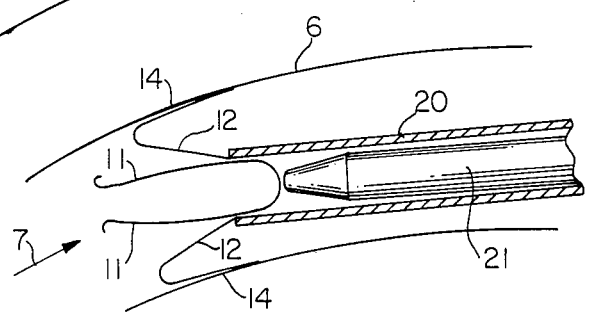

The attraction of choosing legs 12 a little shorter than the legs 11 will now become apparent from the description of FIGS. 7 to 9 which explain the way the filter is positioned. In these drawings, there is once again the vein 6 through which the flow of blood passes in the direction of the arrow 7.

Positioning of the filter is carried out through an insertion tube 20 generally designated in the art as a "Desilet". The filter 10 is pushed through the inside of the tube 20 by a pusher 21.

In FIG. 7, the filter appears with its legs 11 already emerging from the tube 20. It will be noted that the tube 20 is not parallel with the axis of the vein as frequently happens. FIG. 8 shows an instant later when the filter has emerged rather more, the short legs 12 having their rear ends still trapped inside the tube 20 and therefore gripped securely.

It is evident that without the means provided by the invention, a filter left in such a condition would have every chance of becoming hooked in the vein but in a cross-wise position as shown in FIG. 2.

FIG. 9 shows the filter a moment later with its legs 12 which have been freed and which are spread open so that the appendices 14 have become locked fully inside the wall of the vein 6. The longer legs 11 are still trapped in the tube 20. Under these conditions, the filter the action of the flexible legs 12 which are braced on their appendices 14, will automically become substantially positioned in the axis of the vein.

Figure 6:
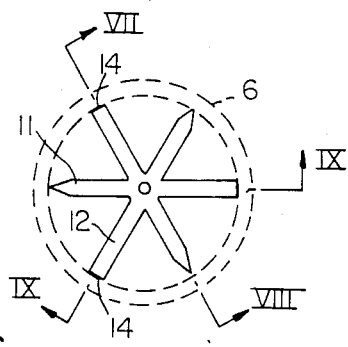
FIG. 6 shows a plan view of FIG. 5, substantially in accordance with the arrow VI in that figure.

An instant later, the legs 11 will be clear of the tube 20 which can be withdrawn and will be in the position shown in FIGS. 5 and 6.

Figure 10:
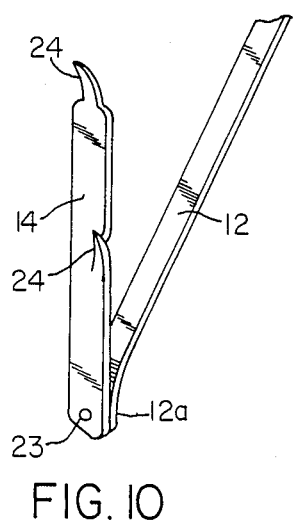
FIG. 10 shows on an enlarged scale a detail of the fitting of an end appendix on one leg of a filter.

Referring now to FIG. 10, this shows on a larger scale how an appendix 14 may be constructed and how it can be fixed towards the free end 12a of a leg 12, for example by a weld 23. If the nature of the material allows, the appendix 14 can be formed by simply folding backwards the end of a longer leg 12, for example a leg which is of the same length as the legs 11. One or a plurality of small hooks 24 may be provided on the appendix 14 to facilitate the locking of the filter and in order to ensure a more positive action of these legs 12 for centering purposes.

It is convenient to note that the appendices 14 may likewise favor satisfactory hooking of the filter in the vein and better tolerance, making it possible in particular to reduce the aggressiveness of the anchoring hooks, by virtue of the larger anchoring surface which these appendices offer.

Figure 11:
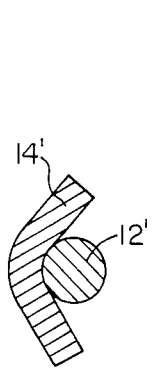
FIGS. 11 and 12 show another detail of fitting of an appendix at the end of a leg of a filter in the event of the leg being made from a circular-section metal wire, FIG. 11 showing a section substantially on the line XI—XI in FIG. 12.
Figure 12:
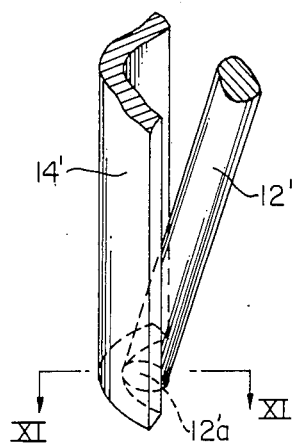

According to FIGS. 11 and 12, a particular shape of appendix 14' is shown in the event of the legs 12' being formed from a round metal wire. In this case, the appendix 14' is cup-shaped or shaped like an open V and the connection may for example be made by electric welding towards the free end 12'a of the wire 12'.

Of course, the invention is by no means confined to the embodiments illustrated and described, the number of legs being capable of variation, both in respect of the legs which carry appendices and also those which do not. The shape and kind of the legs can also vary.

Generally, the legs 12 which carry appendices 14 may be of a length which is less than, equal to or greater than the legs 11 which do not have appendices. However, the ends of the appendices 14 will be set back in relation to the head 13 of the filter so that the appendices are ejected from the positioning tube 20 prior to total release of the filter so that the legs 12 which carry appendices 14 are the first to bear on the inside wall of the vein 6.

I claim:

1. A filter to be positioned within a blood vessel to trap blood clots, said filter comprising:
   a plurality of legs arranged to extend from a head in a substantially conical corolla configuration, each of said legs having a free end; and
   at least some of said legs having respective appendices connected thereto in the region of said free ends thereof, each appendix including a portion extending in the general direction of said head;
   whereby said appendices extend substantially parallel with a wall of the vessel when said filter is inserted within the same.

2. The filter of claim 1, wherein
   each said appendix comprises a free end which is set back with respect to said head.

3. The filter of claim 1, wherein
   said legs extend from said head so as to be expandable from a smaller-diameter conical corolla configuration to a larger-diameter conical corolla configuration.

4. The filter of claim 1, wherein
   three legs comprise said respective appendices and are angularly distributed about an axis of said filter.

5. The filter of claim 1, additionally comprising
   three legs without appendices which are also angularly distributed about the axis of said filter.

6. The filter of claim 1, wherein said appendices comprise
   means for hooking the same onto the wall of the blood vessel.

7. The filter of claim 1, wherein
   said appendices are each constituted by a bent portion at said free end of said respective leg.

8. The filter of claim 1, wherein
   said appendices are each constituted by a separate portion affixed to said free end region of said respective leg.

9. The filter of claim 5, wherein said legs comprising said respective appendices are shorter than said legs without said appendices.

10. The filter of claim 5, wherein said legs comprising said appendices are longer than said legs without said appendices.

11. The filter of claim 5, wherein said legs comprising said appendices and said legs without said appendices are of substantially the same length.

12. The filter of claim 6, wherein
    said hooking means comprise at least one hook situated on each said appendix.

13. The filter of claim 22, wherein said hooking means comprise two hooks situated on each said appendix.

14. The filter of claim 8, wherein at least one of said appendices is constituted by a member welded onto said respective leg.

15. The filter of claim 14, wherein said welded member is cup-shaped or shaped like an open V, and
said respective leg is form from round metal wire.

16. Method for inserting a filter in a blood vessel, comprising the steps of
  inserting a tube containing the filter into the blood vessel, the filter having a plurality of legs extending from a head in a substantially conical corolla configuration, with at least some of the legs having respective appendices connected thereto in the region of free ends thereof, each appendix having a free end extending in the general direction of the head and which is set back with respect to the head; and
ejecting the filter from the tube within the vessel,
whereby the appendices are ejected therefrom prior to total release of the filter, so that the legs having the appendices are the first to bear on an inside wall of the blood vessel, and
the filter is substantially positioned along an axis of the blood vessel.

* * * * *